(12) United States Patent
Lou et al.

(10) Patent No.: US 12,124,973 B1
(45) Date of Patent: Oct. 22, 2024

(54) MODEL-BASED PATIENT ADHERENCE CLASSIFICATION AND INTERVENTION

(71) Applicant: WALGREEN CO., Deerfield, IL (US)

(72) Inventors: Youbei Lou, Grayslake, IL (US); Erik Groves, Deerfield, IL (US); Evie Makris, Deerfield, IL (US); Alexandra Broadus, Deerfield, IL (US)

(73) Assignee: WALGREEN CO., Deerfield, IL (US)

( * ) Notice: Subject to any disclaimer, the term of this patent is extended or adjusted under 35 U.S.C. 154(b) by 503 days.

(21) Appl. No.: 16/583,827

(22) Filed: Sep. 26, 2019

Related U.S. Application Data (60) Provisional application No. 62/857,057, filed on Jun. 4, 2019.

(51) Int. Cl.
*G06N 20/00* (2019.01)
*G06N 5/046* (2023.01)
*G16H 10/60* (2018.01)
*G16H 20/10* (2018.01)
(Continued)

(52) U.S. Cl.
CPC ............. *G06N 5/046* (2013.01); *G06N 20/00* (2019.01); *G16H 10/60* (2018.01); *G16H 20/10* (2018.01); *G16H 50/30* (2018.01); *H04L 67/10* (2013.01)

(58) Field of Classification Search
None
See application file for complete search history.

(56) References Cited

U.S. PATENT DOCUMENTS 8,666,926 B1 * 3/2014 Nease ............... G06N 5/022
706/50
10,108,975 B1 * 10/2018 Benner ............... G06Q 50/22
(Continued)

FOREIGN PATENT DOCUMENTS

WO    WO-2019014717 A1 *  1/2019

OTHER PUBLICATIONS

Abby Connect, How to Return a Missed Call (May 24, 2018), available at https://www.abby.com/blog/how-to-return-a-missed-phone-call/ (last visited on Dec. 23, 2021) (Year: 2018).*
(Continued)

*Primary Examiner* — Jonathon A. Szumny
*Assistant Examiner* — Nicholas Akogyeram, II
(74) *Attorney, Agent, or Firm* — MARSHALL, GERSTEIN & BORUN LLP; Randall G. Rueth (57) ABSTRACT

Systems and methods for using predictive modeling to improve patient adherence to prescription medication regimens are provided. Training data may be generated using historical prescription adherence data associated with a patient population. A prescription adherence machine learning model may be trained using the training data, and the trained model may be applied to current prescription adherence data associated with a patient to predict a likelihood that a proportion of days that the patient will be covered by a prescribed medication will be below a threshold value over a calendar year. A patient risk score may be generated for the patient based at least in part on the predicted likelihood that the proportion of days covered by the prescribed medication will be below the threshold value. Based on the patient's patient risk score, the patient may be automatically contacted for intervention.

14 Claims, 6 Drawing Sheets

(51) Int. Cl.
   *G16H 50/30*       (2018.01)
   *H04L 67/10*       (2022.01)

(56) References Cited

U.S. PATENT DOCUMENTS

| | | | |
|---|---|---|---|
| 2010/0241459 A1* | 9/2010 | Rao | G06Q 30/0203 |
| | | | 705/3 |
| 2012/0101630 A1* | 4/2012 | Daya | G16H 50/20 |
| | | | 700/231 |
| 2016/0321406 A1* | 11/2016 | Timmerman | G06Q 10/10 |
| 2017/0076059 A1* | 3/2017 | Morefield | G16H 50/30 |
| 2017/0116389 A1* | 4/2017 | Matlin | G16H 20/10 |
| 2017/0213007 A1* | 7/2017 | Moturu | G16H 20/10 |
| 2020/0134144 A1* | 4/2020 | Depaolo | G06F 9/54 |
| 2021/0065865 A1* | 3/2021 | Einav | G16H 40/20 |

OTHER PUBLICATIONS

Wei-Hsuan Lo-Ciganic et al., Evaluation of machine-learning algorithms for predicting opioid overdose risk among Medicare beneficiaries with opioid prescriptions, 2 JAMA Network Open (2019) (Year: 2019).*

* cited by examiner

MODEL-BASED PATIENT ADHERENCE CLASSIFICATION AND INTERVENTION

CROSS REFERENCE TO RELATED APPLICATIONS

This application claims the benefit of provisional U.S. Patent Application No. 62/857,057, filed on Jun. 4, 2019, entitled "Model-Based Patient Adherence Classification and Intervention," and is related to commonly-owned U.S. Provisional Application No. 62/857,067, filed on Jun. 4, 2019, entitled "Integrated Portal for Patient Adherence Monitoring and Intervention," the entire contents of each of which are herein incorporated by reference.

FIELD OF THE DISCLOSURE

The present disclosure generally relates to systems and methods for using predictive modeling to improve patient adherence to prescription medication regimens.

BACKGROUND

The background description provided herein is for the purpose of generally presenting the context of the disclosure. Work of the presently named inventors, to the extent it is described in the background section, as well as aspects of the description that may not otherwise qualify as prior art at the time of filing, are neither expressly nor impliedly admitted as prior art against the present disclosure.

Effective management of a patient's medication therapy is an important factor in achieving successful treatment results. The more closely a patient adheres to his or her prescribed medication treatment regimen, the more likely it is that the treatment will be effective. Unfortunately, in many instances patients do not adequately comply with their medication therapy regimens. Poor compliance with treatment regimens can result in negative health impacts for the patient as well as negative impacts on those who have an interest in maintaining the patient's health. For many patients with chronic medical conditions, the key to successful treatment of their conditions is adherence to a doctor-prescribed regimen of prescription medications. The regimen often involves the patient consistently taking his or her prescribed medication every day (or multiple times per day). Thus, a patient must consistently fill his or her prescription every week (or every month, or every two months, etc.) as needed in order to effectively follow the regimen.

However, some patients fail to consistently fill their prescriptions. For example, a patient may fill his or her prescription late, leaving a gap in prescription coverage between the date of the previous prescription fill running out and the date of the subsequent prescription fill. In some cases, these gaps in coverage during which a patient fails to take his or her prescribed medication may cause a preventable hospital admission or doctor visit. Moreover, in some cases, these gaps in coverage may cause a doctor to change unnecessarily (or, conversely, not to change when necessary) the regimen based on insufficient or inaccurate information about a patient's compliance with the regimen.

In some cases, a pharmacy may schedule an intervention including a pharmacist or doctor consultation for a patient who may be at risk of developing complications due to significant gaps in prescription medication coverage. In an intervention, the pharmacist or doctor may meet with a patient to discuss the importance of filling the prescription on time, determine why the patient has not been filling his or her prescription on time, and/or develop a solution that works for the patient.

However, it may be difficult for pharmacies to determine which patients are most at risk of developing complications due to significant gaps in prescription medication coverage until the patient has already experienced a significant gap in coverage. That is, it may be difficult for pharmacies to know whether a patient will fill his or her prescription ten days late one time but otherwise fill the prescription consistently over the course of a year (resulting in ten days total during which the patient is not covered over the course of the year) or whether the patient will fill his or her prescription five days late each month, (resulting in 60 days total during which the patient is not covered over the course of the year). Moreover, a given pharmacy may only have access to a limited number of medical professionals (e.g., pharmacist, doctor, nurse, etc.) qualified to conduct an intervention, and each medical professional may only have a limited amount of time during which to conduct interventions. Consequently, because it may be difficult for pharmacies to determine which patients are most at risk of developing complications due to significant gaps in prescription medication coverage, it may be difficult for a pharmacy to determine how to prioritize patients for intervention based on which patients are most at-risk.

SUMMARY

The present application discloses methods, systems, and computer-readable media storing instructions for using predictive modeling to improve patient adherence to prescription medication regimens. As described herein, the disclosed aspects improve existing prescription adherence systems by using a machine learning model to predict the likelihood a particular patient's proportion of days covered during a current calendar year will be below a threshold value, thereby enabling a pharmacy to determine which patients are most at risk of developing complications due to gaps in prescription medication coverage and schedule patient interventions accordingly. Moreover, in some embodiments, the disclosed aspects improve existing prescription adherence systems by using a machine learning model to predict parameters for an effective patient intervention for a particular patient. Various aspects are summarized below and described in further detail herein.

The present application discloses methods, systems, and computer-readable media storing instructions for using predictive modeling to improve patient adherence to prescription medication regimens. This may include generating, by a processor, training data using historical prescription adherence data associated with a patient population; training, by a processor, a prescription adherence machine learning model using the training data; applying, by a processor, the trained prescription adherence machine learning model to current prescription adherence data associated with a patient to predict a likelihood that a proportion of days that the patient will be covered by a prescribed medication over a predetermined time period (e.g., a calendar year) will be below a threshold value; generating, by a processor, a patient risk score for the patient based at least in part on the predicted likelihood that the proportion of days, over the calendar year, that the patient will be covered by the prescribed medication will be below the threshold value; and automatically attempting, by a processor, to contact the patient for intervention based on the patient's patient risk score.

For example, the prescription adherence data may include data indicating one or more of: (i) a number of days between a patient's expected first prescription fill date of the calendar year and the patent's first prescription fill date of the calendar year, (ii) a month of a patient's first prescription fill date of the calendar year, (iii) a number of days' supply associated with a patient's first prescription fill date of the calendar year, (iv) a proportion of days, over a previous calendar year, that a patient was covered by the prescribed medication, (v) a number of days between a patient's actual first prescription fill date of the previous calendar year and the end of the previous calendar year, (vi) the highest number of consecutive days that a patient was not covered by the prescribed medication during the previous calendar year, and/or (vii) whether a brand of a patient's prescribed medication was changed during the previous calendar year.

Moreover, in some examples, the methods, systems, and computer-readable media storing instructions for using predictive modeling to improve patient adherence to prescription medication regimens may include applying, by a processor, the trained prescription adherence machine learning model to the prescription adherence data associated with the patient to assign the patient to a risk profile group and selecting, by a processor, a mode of communication for attempting to contact the patient based on the risk profile group of the patient.

Furthermore, in some examples, the methods, systems, and computer-readable media storing instructions for using predictive modeling to improve patient adherence to prescription medication regimens may include selecting, by a processor, a type of intervention based on the risk profile group of the patient.

Additionally, in some examples, the patient may be one of a plurality of patients, and the methods, systems, and computer-readable media storing instructions for using predictive modeling to improve patient adherence to prescription medication regimens may include prioritizing, by a processor, each of the plurality of patients based on one or more of the patient risk score or the risk profile group of each of the plurality of patients; and automatically attempting, by a processor, to contact each of the patients for intervention in an order based on the prioritizing. Furthermore, in some examples, prioritizing each of the plurality of patients may be further based on a number of failed contact attempts associated with each of the plurality of patients.

In various embodiments, additional, fewer, or alternate actions may be included or performed by the method, system, and computer-readable medium, including those discussed elsewhere herein.

BRIEF DESCRIPTION OF THE DRAWINGS

The figures described below depict various aspects of the applications, methods, and systems disclosed herein. It should be understood that each figure depicts an embodiment of one or more particular aspects of the disclosed applications, systems and methods, and that each of the figures is intended to accord with one or more possible embodiments thereof. Furthermore, wherever possible, the following description refers to the reference numerals included in the following figures, in which features depicted in multiple figures are designated with consistent reference numerals.

DETAILED DESCRIPTION

Figure 1A:
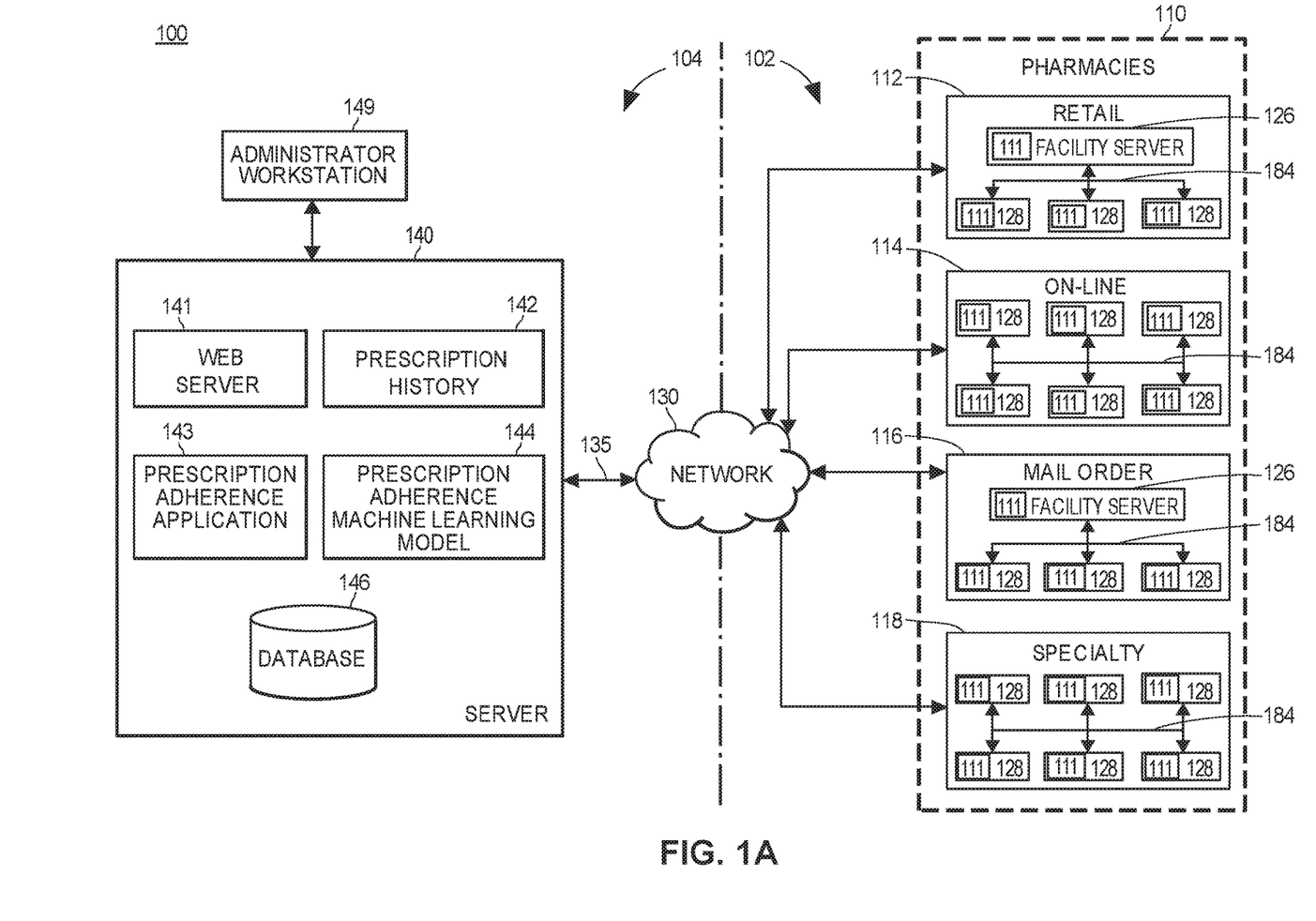
FIGS. 1A-1C illustrate block diagrams of a computer network, a computer server, and computing terminals on which an exemplary prescription adherence system may operate to use predictive modeling to improve patient adherence to prescription medication regimens, in accordance with the embodiments described herein.

FIG. 1A illustrates a block diagram of an exemplary prescription adherence system 100 for using predictive modeling to improve patient adherence to prescription medication regimens, as described in FIGS. 2-4 below. The high-level architecture includes both hardware and software applications, as well as various data communications channels for communicating data between the various hardware and software components. The prescription adherence system 100 may be roughly divided into front-end components 102 and back-end components 104. The front-end components 102 may be disposed within one or more pharmacies 110. Where there is more than one pharmacy 110, the pharmacies 110 may be located, by way of example rather than limitation, in separate geographic locations from each other, including different areas of the same city or different states. The front-end components 102 may comprise a plurality of pharmacy workstations 128. The pharmacy workstations 128 may be local computers located in the various pharmacies 110 that execute a variety of applications related to pharmacy management. Pharmacists, technicians, or other users (not shown) may use the pharmacy workstations 128 to access patient information, enter new prescriptions, access insurance and payment information, and perform other pharmacy management-related tasks. Thus, the front-end components 102 may include pharmacy workstations 128 for servicing patients visiting an in-store retail pharmacy 112, pharmacy workstations 128 for servicing patients who choose to fill their prescriptions through an on-line pharmacy 114, a plurality of pharmacy workstations 128 for servicing patients who prefer to use the services of a mail-order pharmacy 116, and a plurality of pharmacy workstations 128 for servicing patients who require the services of a specialty pharmacy 118.

The front-end components 102 may also comprise a plurality of facility servers 126 disposed at the pharmacies 110, instead of or in addition to a plurality of pharmacy workstations 128. Each pharmacy 112, 114, 116, 118 may include one or more facility servers 126 that may be utilized to facilitate communications between the pharmacy workstations 128 and the back-end components 104 via a network 130, described below, and to store information for a plurality of patients, employees, accounts, or other records associated with each facility. Further, each pharmacy 112, 114, 116, 118 may include one or more pharmacy workstations 128 operatively connected to the facility server 126 via a local network 184.

The front-end components 102 may communicate with the back-end components 104 via the network 130. The network 130 may be a proprietary network, a secure public internet, a virtual private network or some other type of network, such as dedicated access lines, telephone lines, satellite links, cellular data networks, combinations of these, etc. Where the network 130 comprises the Internet, data communications may take place over the network 130 via an Internet communication protocol. The back-end components 104 include one or more servers 140. Each server 140 may include one or more computer processors adapted and configured to execute various software applications and components of the prescription adherence system 100, in addition to other software applications. The server 140 may further include a database 146 that is adapted to store data related to the prescription medication histories of a plurality of patients. Such data may include, for each of a plurality of patients, information regarding one or more original or refill purchases of one or more prescription medications (e.g., first fill dates, refill dates, and last fill dates). Moreover, the data stored in the database 146 may include prescription adherence data and/or intervention data for each of the plurality of patients, as discussed in greater detail with respect to FIGS. 2-4. The server 140 may access data stored in the database 146, as well as data stored in other systems (not shown) when executing various functions and tasks associated with the operation of the prescription adherence system 100.

Although the prescription adherence system 100 is shown to include one server 140 and four pharmacies 112, 114, 116, and 118, it should be understood that different numbers may be utilized. For example, the system 100 may include a plurality of servers 140 and hundreds of pharmacies 110, all of which may be interconnected via the network 130. Furthermore, the database storage or processing performed by the one or more servers 140 may be distributed among a plurality of servers 140 in an arrangement known as "cloud computing." This configuration may provide various advantages, such as enabling near real-time uploads and downloads of information as well as periodic uploads and downloads of information. This may in turn support a thin-client embodiment of the pharmacy workstations 128, wherein most of the processing and storage is performed by the servers 140.

Figure 1B:
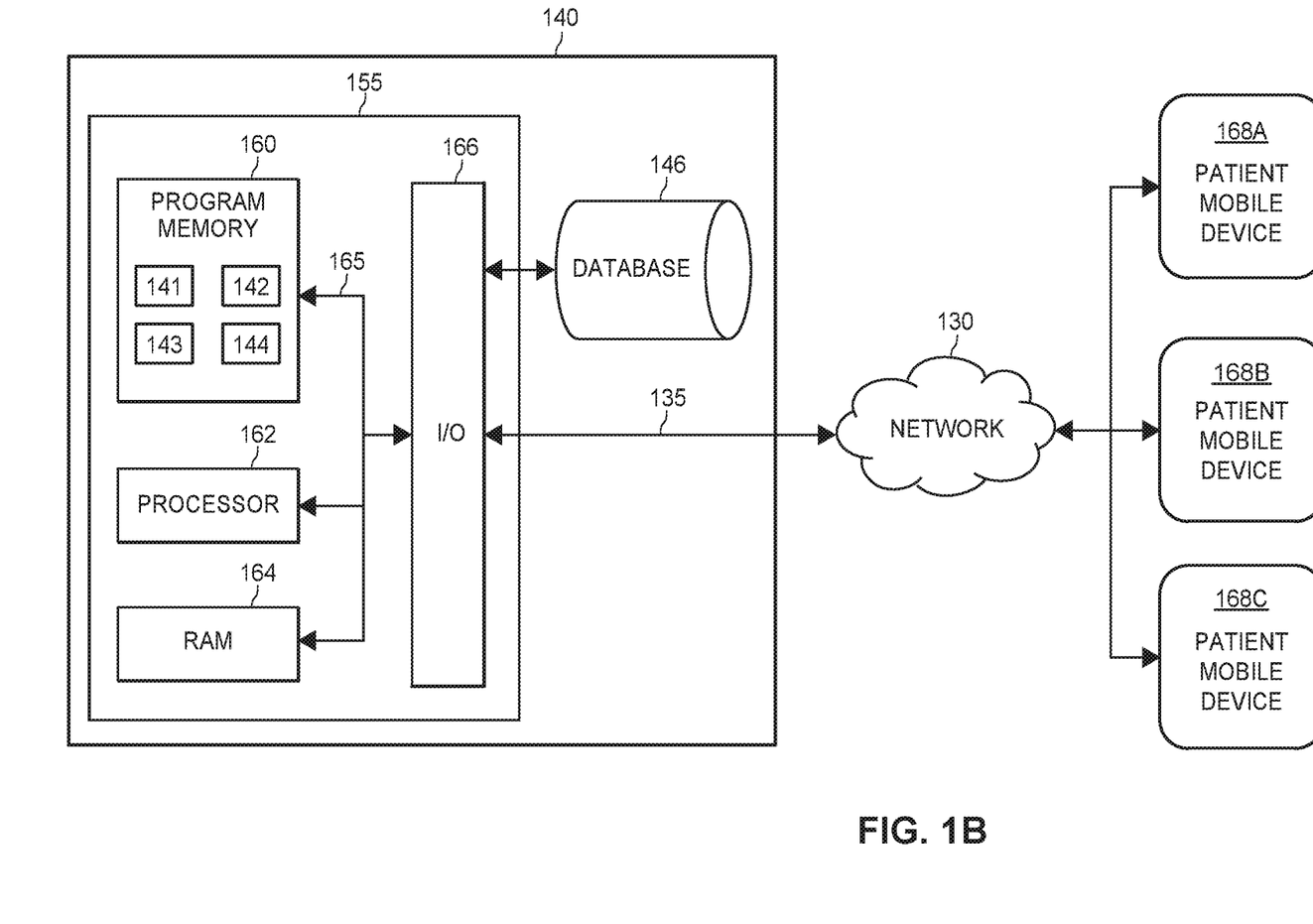

FIG. 1B is a schematic diagram of one possible embodiment of the server 140. The server 140 may have a controller 155 that is operatively connected to the database 146 via a link 156. It should be noted that, while not shown, additional databases may be linked to the controller 155 in a known manner. The controller 155 may include a program memory 160, a processor 162 (which may be called a microcontroller or a microprocessor), a random-access memory (RAM) 164, and an input/output (I/O) circuit 166, all of which may be interconnected via an address/data bus 165. It should be appreciated that although only one processor 162 is shown, the controller 155 may include multiple processors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM 164 and program memories 160 may be implemented as semiconductor memories, magnetically readable memories, or optically readable memories, for example. The controller 155 may also be operatively connected to the network 130 via a link 135. In some examples, the server 140 may communicate with one or more patient mobile devices 168A, 168B, 168C, etc. via the network 130. These patient mobile devices may be, e.g., personal computers, portable devices such as tablet computers or smartphones, wearable computing devices, etc. associated with various patients.

Figure 1C:
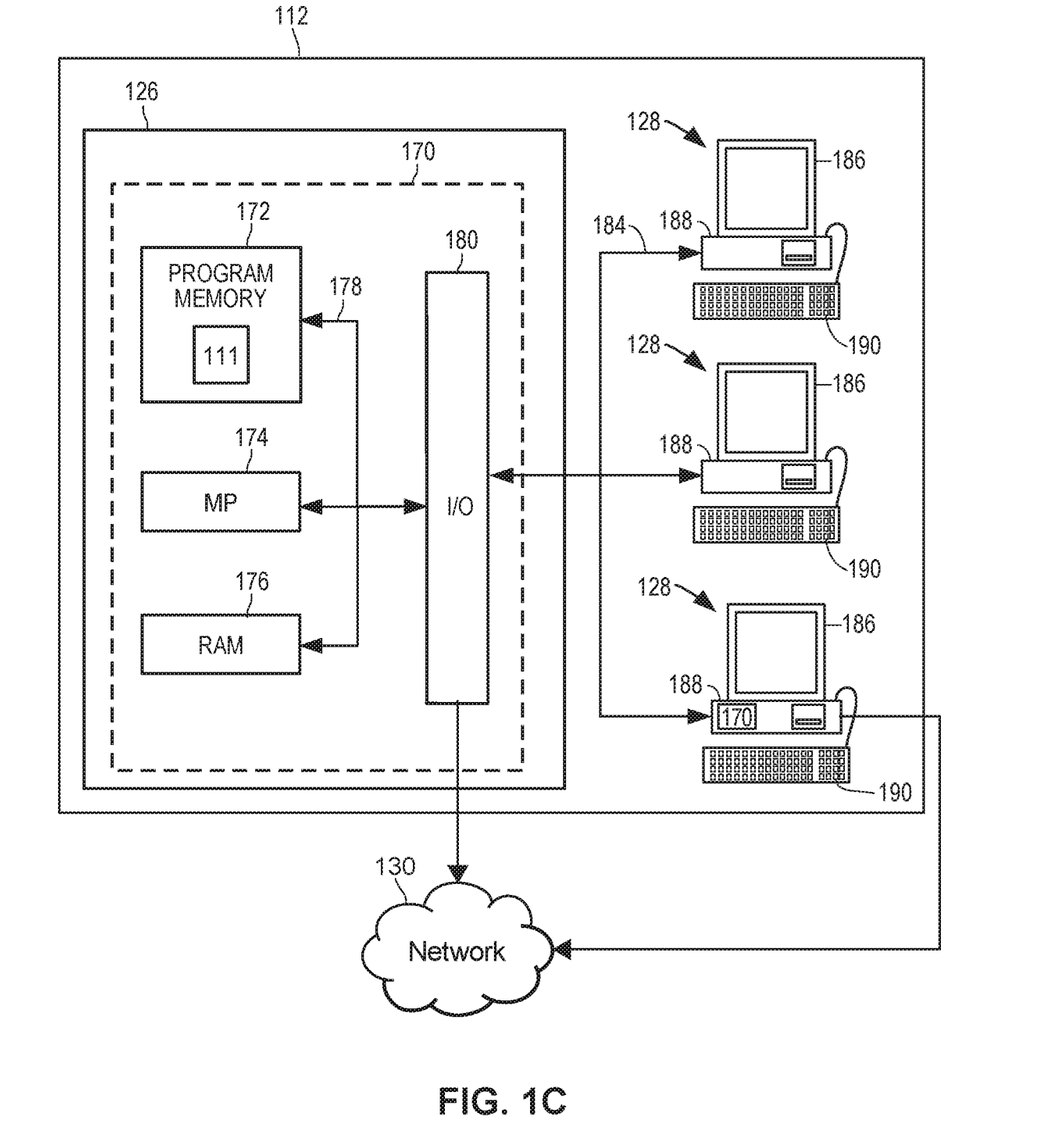

FIG. 1C is a schematic diagram of one possible embodiment of the front-end components 102 located in one or more of the pharmacies 110 from FIG. 1A, such as pharmacy 112. Although the following description addresses the design of the pharmacies 110, it should be understood that the design of one or more of the pharmacies 110 may be different than the design of other pharmacies 110. Also, each of the pharmacies 110 may have various different structures and methods of operation. It should also be understood that the embodiment shown in FIG. 1C illustrates some of the components and data connections present in an exemplary pharmacy 112, however it does not illustrate all of the data connections present in a typical pharmacy. For exemplary purposes, one design of a pharmacy is described below, but it should be understood that numerous other designs may be utilized.

Each pharmacy 110 may have one or more pharmacy workstations 128 or one or more facility servers 126. The facility server 126 may be operatively connected to a plurality of pharmacy workstations 128 via a network 184. The network 184 may be a wide area network (WAN), a local area network (LAN), or any other type of network readily known to those persons skilled in the art. The facility server 126 or workstations 128 may also be operatively connected to the server 140 via the network 130.

Each workstation 128 or facility server 126 includes a controller 170. Similar to the controller 155 from FIG. 1B, the controller 170 may include a program memory 172, a microcontroller or a microprocessor (MP) 174, a random-access memory (RAM) 176, and an input/output (I/O) circuit 180, all of which may be interconnected via an address/data bus 178. As discussed with reference to the controller 155, it should be appreciated that although only one microprocessor 174 is shown, the controller 170 may include multiple microprocessors 174. Similarly, the memory of the controller 170 may include multiple RAMs 176 and multiple program memories 172. Although the I/O circuit 180 is shown as a single block, the I/O circuit 180 may include a number of different types of I/O circuits. The RAM 176 and programs memories 172 may also be implemented as semiconductor memories, magnetically readable memories, and/or optically readable memories, for example. In some embodiments, the RAM 176 and program memories 172 may be combined into one memory without materially altering the system 100 as described herein.

The workstations 128 may further include displays 186 and keyboards 190, as well as a variety of other input/output devices (not shown) such as scanners, printers, touch screens, track pads, track balls, voice recognition systems, digital cameras, etc. Pharmacists, technicians, or other users may sign on to the pharmacy workstations 128 using any available technique, such as entering a user name and password. If users are required to sign on to the pharmacy workstations 128, this information may be passed via the network 184 to the facility server 126, so that the controller 170 will be able to identify which users are signed on to the system.

In one embodiment, the prescription adherence system 100 may utilize a web interface to enable communication between the pharmacies 110 and the server 140, in which case the server 140 may include a web server 141. The web server 141 may be a stand-alone server, or a software module implemented within the server 140. The various front-end components 102 may include a web browser client application 111 to communicate with the back-end components 104. A web server 141 may transmit web pages to the facility servers 126 and pharmacy workstations 128 in response to URL requests received by the web server 141 from the front-end components 102 over the network 130. The web pages sent to the front-end components 102 may include data in the database 146. It should be noted that, while the current embodiment describes a web server 141 and a web browser client 111, each implementing the hyper-text transfer protocol, the web server 141 could implement any known or later-developed protocol compatible with the web browser client application 111 running on the front-end components 102 and adapted to the purpose of receiving and providing the necessary patient information via the network 130.

The server 140 may further include a number of software applications stored in a program memory 160. The software applications may be executed on the same computer processor as the web server application 141, or on different processors. The various software applications may include a prescription history module 142 for accessing information regarding the medical history of a patient, including medicines prescribed and prescriptions dispensed. The prescription history module 142 may request or receive data from the database 146 or other sources of information regarding the patient (not shown). Such other sources may include third-party databases of information regarding the medical histories of patients, including data regarding prescriptions filled at pharmacies (not shown) other than the pharmacies 110. Such other sources may further include databases of general demographic information concerning the patient, the pharmacy 110, or one or more third-party payors or other interested third parties. If part or all of the information is stored in a legacy data system (not shown), the prescription history module 142 may access the legacy data system (not shown) to obtain information regarding the patient, the patient's prescription medication and other medical history, or other relevant information.

The software applications may further include a prescription adherence application 143 for training a prescription adherence machine learning model 144; using the trained prescription adherence machine learning model 144 to predict a likelihood that a particular patient's proportion of days covered by a prescribed medication will be below a threshold value and/or to predict parameters for an effective patient intervention for a particular patient; calculating a risk score and/or a risk profile for the patient based on these predictions; and/or automatically attempting to contact the patient for an intervention based on one or more of the patient's patient risk score and/or patient risk profile. For example, automatically contacting the patient for the intervention may include causing a printer communicatively connected to the server 140 to print a postcard reminder addressed to the patient for scheduling the intervention. As another example, automatically contacting the patient for the intervention may include automatically sending a text message or a phone message to a mobile device 168A, 168B, 168C associated with the patient (e.g., as shown in FIG. 1B). As still another example, automatically contacting the patient for the intervention may include posting a message in a web portal account associated with the patient. Those of ordinary skill in the art will appreciate that these modules may be implemented in any number of modules; their functions need not be divided as indicated in FIG. 1A.

Finally, the back-end components 104 may include one or more administrator workstations 149. The administrator workstation 149 allows an authorized user to access the various applications running on the server 140 to alter or adjust the operation of the prescription adherence system 100. For example, a regulatory agency may change its rules regarding the use of patient medical records. The administrator may then access the server 140 via the administrator workstation 149 and alter rules active in the modules 142-144 to reflect the changes in regulatory or interested third party rules.

For purposes of implementing the prescription adherence system 100, the primary point of contact with the patient is through a pharmacy 110. The pharmacist filling the prescription will have access to one of the pharmacy workstations 128 and may invoke the prescription adherence system 100 when he or she fills the patient's prescription. Alternatively, the prescription adherence system 100 may be invoked automatically for each new prescription entered or by a broader system, such as a medication management system. As an additional alternative, the prescription adherence system 100 may be invoked on a periodic basis (e.g., monthly or annually) for batches of patients, such as based upon prescription medication or payor. In some embodiments, the prescription adherence system 100 may be accessed by one or more additional computing devices (not shown) via the network 130 to generate and display reports regarding patient adherence for one or more patients.

Figure 2:
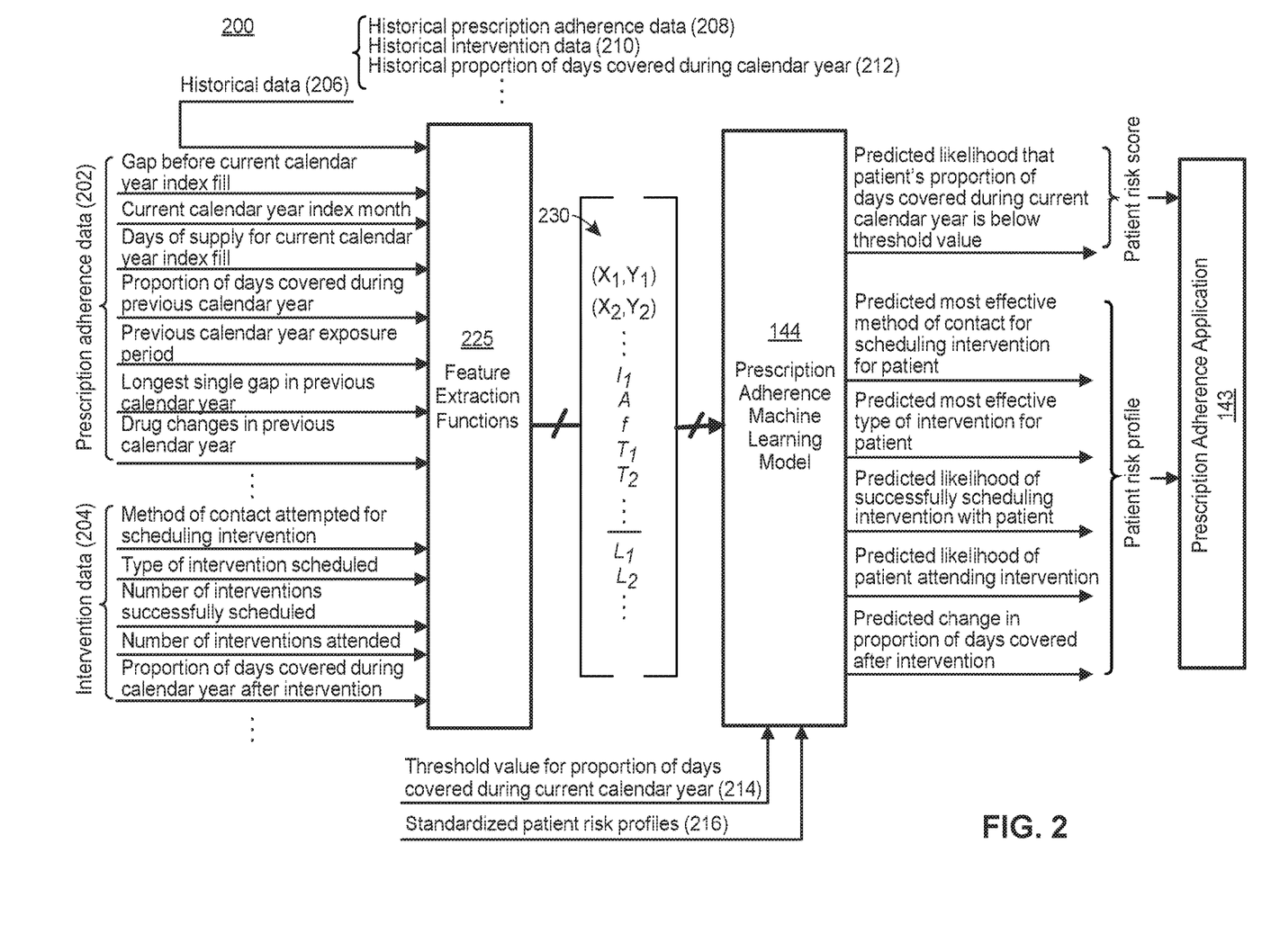
FIG. 2 illustrates a block diagram of an example prescription adherence machine learning model which the prescription adherence system of FIG. 1 can use to predict a likelihood that a particular patient's proportion of days covered by a prescribed medication will be below a threshold value and/or to predict parameters for an effective patient intervention for a particular patient, in accordance with the embodiments described herein.

Now referring to FIG. 2, as discussed above, the prescription adherence application 143 may train and operate the prescription adherence machine learning model 144 in accordance with the scheme 200. The prescription adherence application 143 can receive various input signals, including prescription adherence data 202 for a patient, intervention data 204 for a patient, historical data 206 for a patient population (e.g., including historical prescription adherence data 208, historical intervention data 210, and an indication of historical proportions of days covered during each calendar year for each patient 212, etc.), various threshold values 214, various standardized patient risk profiles 216, etc., e.g., from the database 146 as shown in FIGS. 1A and 1B. Although discussed as relating to calendar years for clarity, the model may be trained for any predetermined period of time in various embodiments.

For example, the prescription adherence data 202 and historical prescription adherence data 208 may include, for a plurality of patients, data associated with each patient's prescription medication coverage during a given calendar year as well as previous calendar years. For instance, as a few examples, the prescription adherence data 202 and/or historical prescription adherence data 208 may include, for a particular patient during a particular calendar year, an indication of a gap in prescription medication coverage before the patient's first prescription fill of that calendar year, an indication of the month of the patient's first prescription fill of that calendar year, the days' supply of the patient's first prescription fill of that calendar year, the proportion of days of the previous calendar year that the patient was covered by his or her prescribed medication, the total number of days during the previous calendar year that the patient was not covered by his or her prescribed medication, the longest single gap in coverage during the previous calendar year, any drug changes during the previous calendar year, etc.

Moreover, the intervention data 204 and historical intervention data 210 may include, for each patient of a given patient population, data associated with any interventions that were scheduled for and/or attended by the patient during a given calendar year as well as over previous calendar years. For instance, as a few examples, the intervention data 204 and/or historical intervention data 210 may include, for a particular patient, the methods of contact that were used to schedule any interventions with that patient in various years, the types of interventions that were scheduled for the patient during various years, the number of interventions that were successfully scheduled for the patient during various years, the number of interventions that were actually attended by the patient during various years, the number of days that a patient was covered by his or her prescribed medication after any interventions (including, e.g., comparisons of numbers of days a patient was covered before the intervention versus after the intervention), etc.

Generally speaking, the feature extraction functions 225 can operate on at least some of these input signals to generate feature vectors, or logical groupings of parameters associated with certain patients over certain periods of time. For example, the feature extraction functions 225 may generate a feature vector that indicates that, for a patient with less than 30 days' supply in his or her first prescription fill of a given year, the result corresponds to higher proportion of days covered during that year compared to patients with more than 30 days' supply in their first prescription fill of the year. As another example, the feature extraction functions 225 may generate a feature vector that indicates that, for a patient with a gap of 10 days or more in February of a given year, the result corresponds to a higher responsiveness to an in-person consultation from a pharmacist than to a phone consultation from the pharmacist. As still another example, the feature extraction functions 225 may generate a feature vector that indicates that, for a patient who actually attended an intervention that was scheduled in a previous year, the result corresponds to a higher likelihood that the patient will attend an intervention that is scheduled in the current year as compared to patients who did not attend an intervention scheduled in a previous year. These results can be used as a set of labels for the feature vectors.

Accordingly, the feature extraction functions 225 can generate feature vectors 230 using the prescription adherence data 202 for a patient, intervention data 204 for the patient, and/or historical data 206. The prescription adherence application 143 may further receive input signals associated with certain threshold values 214 and standardized patient risk profiles 216, etc.

In general, the prescription adherence application 143 can train the prescription adherence machine learning model 144 using supervised learning, unsupervised learning, reinforcement learning, or any other suitable technique. Moreover, the prescription adherence application 143 can train the prescription adherence machine learning model 144 as a standard regression model. Specifically, the prescription adherence application 143 can train the prescription adherence machine learning model 144 using the generated feature vectors 230 as well as inputs such as, e.g., certain threshold values 214 and standardized patient risk profiles 216. Because the prescription adherence application 143 generally does not modify the various threshold values 214 and various standardized patient risk profiles 216, during training, these inputs can be considered hyperparameters.

Over time, as the prescription adherence application 143 trains the prescription adherence machine learning model 144, the prescription adherence machine learning model 144 can learn to predict a likelihood that patient's proportion of days covered during the current calendar year will below a threshold value based on prescription adherence data 202 associated with a patient. For example, the prescription adherence machine learning model 144 may identify that, for a particular patient, the likelihood that the patient's proportion of days covered in 2019 will be less than the threshold value will be 50% based on both the fact that the patient's first prescription fill of 2019 was for a prescription with less than 30 days' supply and based on the fact that the patient's proportion of days covered in 2018 was less than the threshold value.

The prescription adherence machine learning model 144 may further learn to identify parameters that are likely to lead to an effective intervention for the patient based on prescription adherence data 202 associated with a patient and/or the intervention data 204 associated with the patient. For instance, for a given patient, the prescription adherence machine learning model 144 may predict the most effective method of contact for scheduling an intervention, the most effective type of intervention, the likelihood of successfully scheduling an intervention, the likelihood of the patient attending the intervention, a predicted change in the proportion of days that the patient will be covered by his or her prescribed medication after intervention (e.g., opposed to before), etc.

For example, the prescription adherence machine learning model 144 may predict that, based on the patient's longest gap in prescription coverage during 2018's being 20 days and based on a drug change from brand name to generic that the patient experienced during 2018, the patient is likely to be most responsive to an intervention that involves a consultation with a doctor. As another example, the prescription adherence machine learning model 144 may predict, based on an intervention that was scheduled but not attended by a patient during 2018, the patient's total exposure period during 2018, and a gap of two weeks before the patient's first prescription fill of 2019, that the most effective method of scheduling an intervention in 2019 will be via text messaging.

The prescription adherence machine learning model 144 may send indications of the predicted likelihood that the patient's proportion of days covered in the current calendar will be less than the threshold value, as well as indications of parameters that are likely to lead to an effective intervention for the patient to the prescription adherence application 143, where they can be used, e.g., to calculate a risk score for the patient and/or to assign the patient to a patient risk group. Accordingly, the patient's risk score and/or patient risk group may be used to determine, e.g., whether an intervention should be scheduled for the patient, a priority level for the patient's intervention, how best to contact that patient to schedule the intervention, and what type of intervention may be best suited for the patient's needs.

As new prescription adherence data and new intervention data is collected, new training data can be generated and used in subsequent training of the prescription adherence machine learning model 144, i.e., for fine-tuning to improve the performance of the prescription adherence machine learning model 144.

Figure 3:
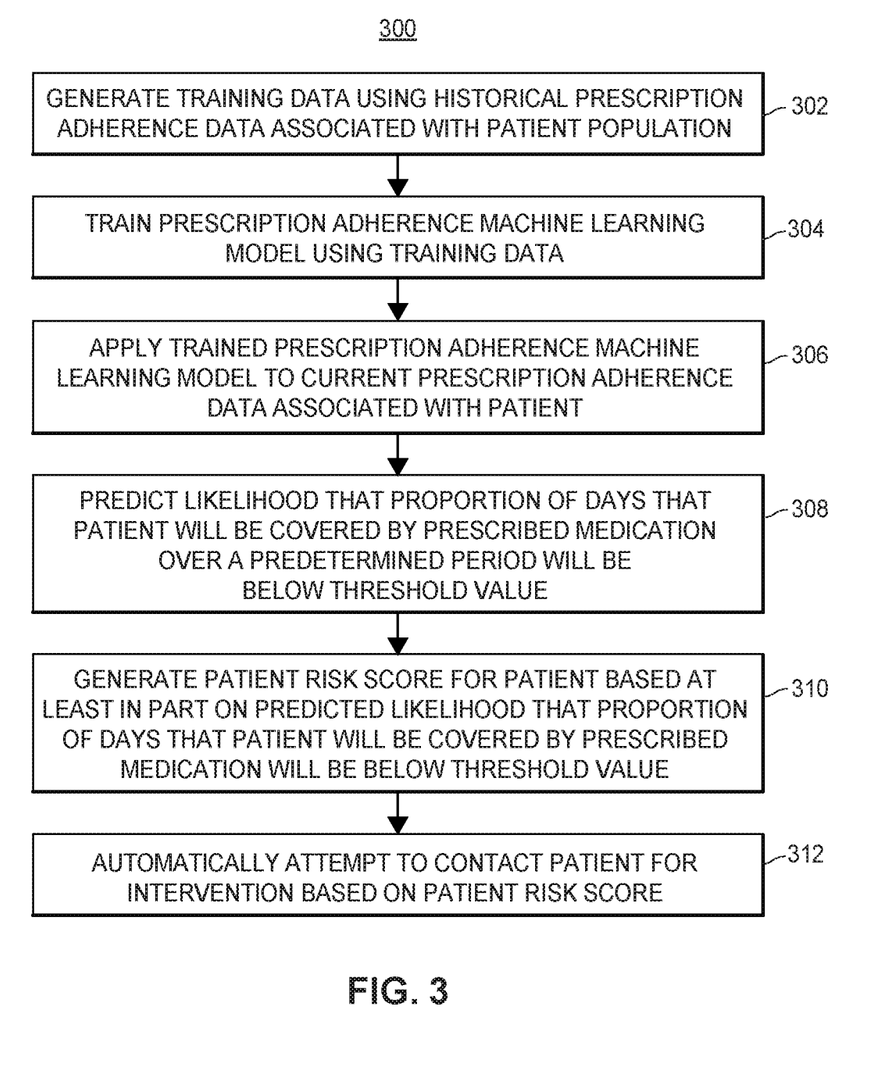
FIG. 3 illustrates a flow diagram of an exemplary computer-implemented method of using predictive modeling to improve patient adherence to prescription medication regimens, in accordance with the embodiments described herein.

Referring now to FIG. 3, a flow diagram of an exemplary computer-implemented method 300 of using predictive modeling to improve patient adherence to prescription medication regimens is illustrated, in accordance with some embodiments. The method 300 can be implemented as a set of instructions (e.g., to be performed by the prescription adherence application 143) stored on a computer-readable memory and executable on one or more processors.

Training data may be generated (block 302) using historical prescription adherence data associated with a patient population. The historical prescription adherence data for the patient population data may be obtained from pharmacy records. The historical prescription adherence data associated with the patient population may include several data points for each patient of the patient population.

For instance, prescription adherence data may include an indication of the number of days between the patient's expected first prescription fill date of the calendar year and the patent's first prescription fill date of the calendar year (also sometimes called the "index fill"). For example, if the calendar year in question were 2019, and the patient was supposed to fill his or her first prescription of 2019 on Jan. 1st of 2019, but actually filled the prescription on Jan. 15th of 2019, the number of days would be 14.

Additionally, prescription adherence data may include an indication of the month of the patient's first prescription fill date of the calendar year, i.e., whether the patient first actually filled their prescription in January, February, March, etc. of a given calendar year. Furthermore, the historical prescription adherence data may include an indication of the number of days' supply associated with the patient's first prescription fill date of the calendar year. For example, if the patient's first prescription fill of a given calendar year was for 90 pills, with instructions to take two pills per day, the number of days' supply would be 45 days.

Additionally, prescription adherence data may include an indication of the proportion of days, over previous calendar years, that the patient was covered by his or her prescribed medication. For instance, if the patient was two weeks late filling a prescription in March 2018, three weeks late filling a prescription in July 2018, and 10 days late filling a prescription in September 2018, there would be 45 days in 2018 during which the patient was not covered by his or her prescribed medication out of 365 days total in 2018, so the proportion of days covered for 2018 would be (365−45)/365=87%.

Moreover, prescription adherence data may include an indication of the number of days between the patient's actual first prescription fill date of the previous calendar year and the end of the previous calendar year. E.g., if the patient's first prescription fill date of 2018 were December $1^{st}$, and the last day of 2018 were December $31^{st}$, the number of days would be 31 days.

Additionally, prescription adherence data may include an indication of the highest number of consecutive days that the patient was not covered by his or her prescribed medication during a previous calendar year, i.e., the "longest gap" during the previous calendar year. For instance, if the patient was two weeks late filling a prescription in March 2018, three weeks late filling a prescription in July 2018, and 10 days late filling a prescription in September 2018, the longest gap during 2018 would be the three weeks in July 2018, i.e., 21 days. Furthermore, the historical prescription adherence data may include an indication of whether the brand of each patient's prescribed medication was changed during the previous calendar year, e.g., from a name brand to a generic, or between brands.

In some embodiments, additional training data may be generated based on historical intervention data for each patient of the patient population. For example, the intervention data may include an indication of whether a patient was selected for intervention in a given calendar year. Additionally, the intervention data may include an indication of a method of contact that was used to contact the patient to schedule the intervention. For example, in some instances, a patient may be contacted via mail, while in other instances, a patient may be contacted via a phone call. In still other instances, a patient may be contacted via email or via text message. Additionally, in some instances, a patient may be contacted via a designated patient portal, e.g., associated with a pharmacy, a medical provider, an insurer, etc.

Additionally, the intervention data may include an indication of a type of intervention scheduled for each patient. For example, an intervention may be a pharmacist intervention or a doctor intervention. Moreover, an intervention be held in various settings, e.g., an in-home consultation, a pharmacy consultation, a phone consultation, a video-conference consultation, etc. Additionally, topics of discussion during an intervention may vary. For example, one patient's intervention may involve a discussion of finances and may include providing financial resources for the patient, while another patient's intervention may involve consultation regarding the potential medical effects of gaps in prescription medication coverage, and still another patient's intervention may involve consultation regarding obtaining insurance and/or contacting insurance providers for coverage.

Furthermore, intervention data may include an indication of whether an intervention was successfully scheduled for a patient and/or a number of interventions that have been scheduled for the patient, e.g., during a calendar year. Additionally, intervention data may include an indication of whether an intervention was actually attended by the patient, and/or a number of interventions attended by the patient, e.g., during a calendar year. Moreover, intervention data may include an indication of the proportion of days in which the patient was covered by his or her prescribed medication during the calendar year of the intervention, and/or an indication of a change in the proportion of days in which the patient was covered by his or her prescribed medication after the patient attended the intervention.

A prescription adherence machine learning model 144 may be trained (block 304) using the training data, as described in greater detail above with respect to FIG. 2. The trained prescription adherence machine learning model 144 may be applied (block 306) to current prescription adherence data and/or current intervention data associated with a particular patient.

By applying the trained prescription adherence machine learning model 144 to the current prescription adherence data and/or the intervention data associated with the patient, a likelihood that the proportion of days that the patient will be covered by his or her prescribed medication over a predetermined time period (e.g., a calendar year) will be below a threshold value may be predicted (block 308). For example, the threshold value may be 80% (or 75%, or 60%, or any other suitable threshold value). Accordingly, the prescription adherence machine learning model 144 may be applied to prescription adherence data associated with a particular patient to determine the likelihood that the patient will be covered by his or her prescribed medication for less than 80% of the current calendar year. For instance, there may be a 90% likelihood that Patient A will be covered by his or her prescribed medication for less than 80% of the 2019 calendar year, while there may be a 20% likelihood that Patient B will be covered by his or her prescribed medication for less than 80% of the 2019 calendar year.

A patient risk score may be generated (block 310) for the patient based at least in part on the predicted likelihood that the proportion of days that the patient will be covered by the prescribed medication over a predetermined time period will be below the threshold value. The risk score may be a scaled score, e.g., on a scale from 1 to 10. A higher risk score may indicate a greater likelihood of the patient being covered by his or her prescribed medication for a proportion of days that is below the threshold value, while a lower risk score may indicate a lesser likelihood of the patient being covered by his or her prescribed medication for a proportion of days that is below the threshold value. For example, using the example above, if there is a 90% likelihood that Patient A will be covered by his or her prescribed medication for less than 80% of the 2019 calendar year, while there is a 20% likelihood that Patient B will be covered by his or her prescribed medication for less than 80% of the 2019 calendar year, a risk score of 9 may be generated for Patient A, while a risk score of 2 may be generated for Patient B.

An attempt may be made to automatically contact (block 312) the patient for intervention based on the patient's patient risk score. In some examples, patients with a risk score above a certain value (e.g., a risk score of 5 or greater on a scale from 1 to 10) may be automatically contacted for intervention, while patients with a risk score below that value may not be automatically contacted for intervention.

Moreover, in some examples, patients may be prioritized based at least in part on their risk scores, and may be automatically contacted for intervention in an order based on the prioritization. For example, a patient with a risk score of 8 may be prioritized over a patient with a risk score of 6. Accordingly, the patient with the risk score of 8 may be automatically contacted for intervention before a patient with a risk score of 6. Moreover, if attempts to contact a patient for intervention are unsuccessful, the patient may be temporarily prioritized below patients who have not been contacted yet (e.g., for one day, for one week, for one month, etc.). For example, an attempt may be made to contact a patient with the risk score of 9, but if he or she cannot be reached, an attempt may be made to contact a "lower priority" patient with a risk score of 7, and the patient with the risk score of 9 may be contacted again at a later time (e.g., after one day, after one week, after one month, etc.)

In some examples, there may be a limited number of time slots available for interventions. For instance, when an intervention involves an in-person consultation or a phone call with a pharmacist, the number of time slots available for interventions may be based on the number of pharmacists (or other medical professionals, such as doctors or nurses) available at a patient's pharmacy and their respective schedules. In these examples, intervention time slots may be provided to patients in an order based on the prioritization described above.

Figure 4:
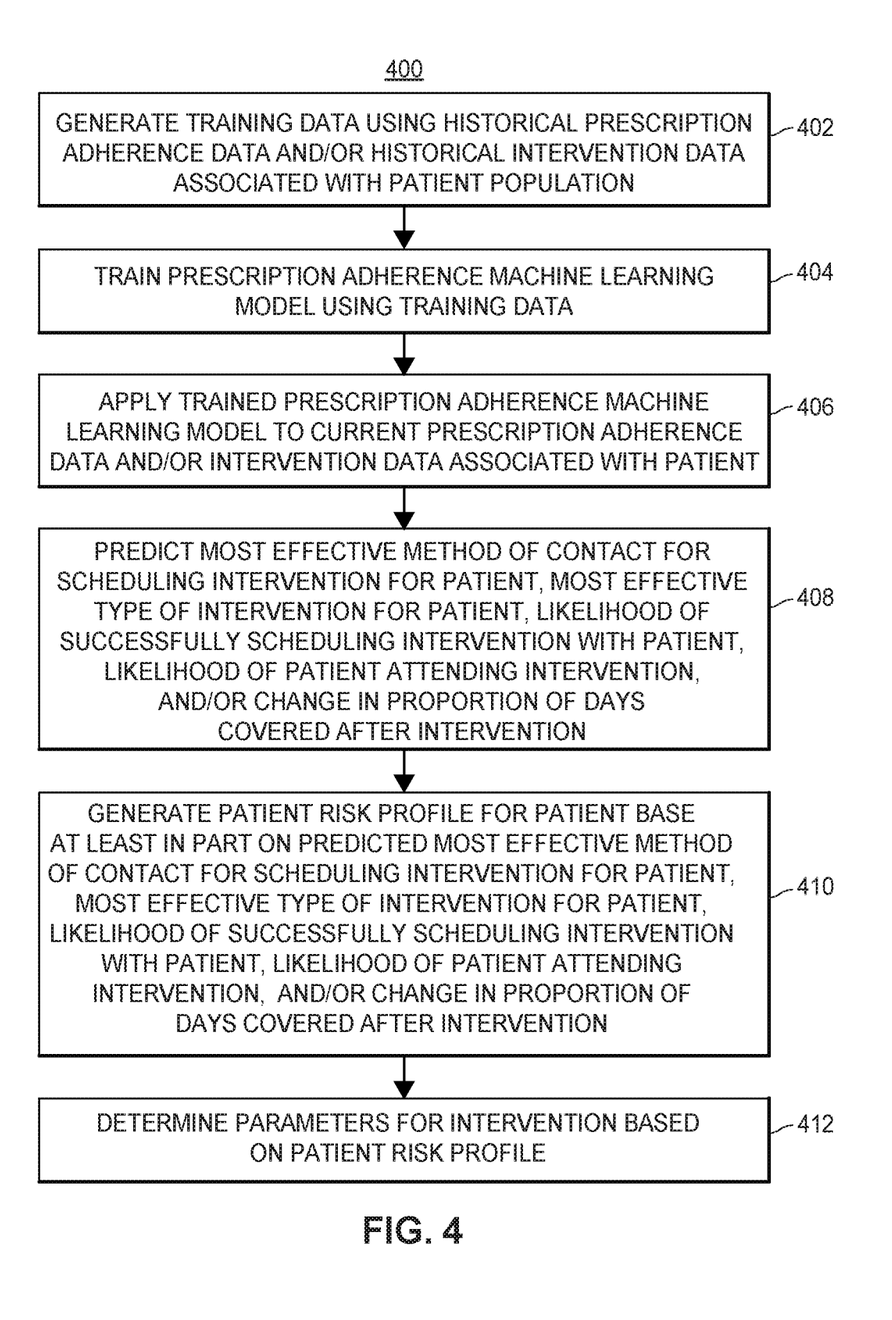
FIG. 4 illustrates a flow diagram of an exemplary computer-implemented method 300 of using predictive modeling to predict parameters for an effective patient intervention for a particular patient, in accordance with the embodiments described herein.

Referring now to FIG. 4, a flow diagram of an exemplary computer-implemented method 400 of using predictive modeling to predict parameters for an effective patient intervention for a particular patient is illustrated, in accordance with some embodiments. The method 400 can be implemented as a set of instructions (e.g., to be performed by the prescription adherence application 143) stored on a computer-readable memory and executable on one or more processors.

Training data may be generated (block 402) using historical prescription adherence data and historical intervention data associated with a patient population, e.g., as discussed above with respect to FIG. 3. A prescription adherence machine learning model 144 may be trained (block 404) using the training data, as described in greater detail above with respect to FIG. 2. The trained prescription adherence machine learning model 144 may be applied (block 406) to current prescription adherence data and/or current intervention data associated with a particular patient.

By applying the trained prescription adherence machine learning model 144 to the current prescription adherence data and/or current intervention data associated with the patient, various factors relating to potential intervention may be predicted (block 408). For example, the most effective method of contact for scheduling an intervention for the patient may be predicted. For instance, some patients may be more likely to schedule an intervention if contacted by mail, while other patients may be more likely to schedule an intervention if contacted via text message, while still other patients may be more likely to schedule an intervention if contacted via phone, other patients may be more likely to schedule an intervention if contacted via a patient portal, etc.

Additionally, the most effective type of intervention for the patient may be predicted. For example, some patients may be more likely to increase their proportion of days covered by their prescribed medication over a calendar year after a pharmacist intervention, while other patients may be more likely to increase their proportion of days covered by their prescribed medication over a calendar year after a doctor intervention. Moreover, some patients may be more likely to increase their proportion of days covered by their prescribed medication over a calendar year after an in-home consultation, while other patients may be more likely to increase their proportion of days covered by their prescribed medication over a calendar year after a phone consultation or a pharmacy consultation. Furthermore, some patients may be more likely to increase their proportion of days covered by their prescribed medication over a calendar year after a consultation regarding finances, while other patients may be more likely to increase their proportion of days covered by their prescribed medication over a calendar year after a consultation regarding the potential medical effects of gaps in prescription medication coverage.

Moreover, the likelihood of successfully scheduling an intervention with the patient and/or the likelihood of the patient attending a scheduled intervention may be predicted. For instance, some patients may be more or less likely to ignore attempts that are made to contact the patient, or may be likely to cancel or no-show a scheduled intervention.

Furthermore, a projected change in proportion of days covered after the intervention may be predicted for the patient. For instance, one patient may change from 50% of days covered by his or her prescribed medication during a calendar year before an intervention to 90% of days covered by his or her prescribed medication during a calendar year after an intervention, while another patient may change from 70% of days covered by his or her prescribed medication during a calendar year before an intervention to 85% of days covered by his or her prescribed medication during a calendar year after an intervention.

Based on the various factors relating to potential intervention that are predicted for the patient, a patient risk profile may be generated (block 410) for the patient. In some examples, the patient risk profile may be selected from a number of standardized patient risk profile groups. Moreover, in some examples, the prescription adherence machine learning model 144 may assign the patient to one of these standardized risk profile groups.

Based on the patient's risk profile, parameters for a patient intervention may be determined (412) for the patient. For example, when a patient is automatically contacted for intervention based on his or her risk score (e.g., as described above with respect to block 312) the patient's risk profile may be used to determine a method of contacting the patient (e.g., based on the likelihood of success for that patient) and/or a type of intervention for the patient (e.g., based on the effectiveness for that patient).

Moreover, in examples in which patients are prioritized (e.g., as described above with respect to block 312), the prioritization may be based on both the patient's risk score and the patient's risk profile. In some instances, the patient's risk score and aspects of the patient's risk profile may be weighted in order to effectively prioritize each patient. For example, a patient with a risk score of 8 but a high likelihood of canceling or no-showing a scheduled intervention may be prioritized below a patient with a risk score of 7 but a low likelihood of canceling or no-showing the scheduled intervention.

Although the foregoing text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the terms "coupled," "connected," "communicatively connected," or "communicatively coupled," along with their derivatives. These terms may refer to a direct physical connection or to an indirect (physical or communication) connection. For example, some embodiments may be described using the term "coupled" to indicate that two or more elements are in direct physical or electrical contact. The term "coupled," however, may also mean that two or more elements are not in direct contact with each other, but yet still co-operate or interact with each other. Unless expressly stated or required by the context of their use, the embodiments are not limited to direct connection.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless the context clearly indicates otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

Upon reading this disclosure, those of skill in the art will appreciate still additional alternative structural and functional designs for system and a method for using predictive modeling to improve patient adherence to prescription medication regimens. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

Finally, the patent claims at the end of this patent application are not intended to be construed under 35 U.S.C. § 112(f), unless traditional means-plus-function language is expressly recited, such as "means for" or "step for" language being explicitly recited in the claims. The systems and methods described herein are directed to an improvement to computer functionality, and improve the functioning of conventional computers.

What is claimed is:

1. A computer-implemented method of using predictive modeling to improve patient adherence to prescription medication regimens, comprising:

generating, by a processor, training data using historical prescription adherence data and parameters of historical interventions to improve patient adherence to prescription medication regimens associated with a plurality of historical patients, and a corresponding proportion of days that each respective historical patient of the plurality of historical patients is covered by their respective prescribed medication over a calendar year, wherein the historical prescription adherence data includes data indicating one or more of: (i) a number of days between a patient's expected first prescription fill date of the calendar year and the patent's first prescription fill date of the calendar year, (ii) a month of a patient's first prescription fill date of the calendar year, (iii) a number of days' supply associated with a patient's first prescription fill date of the calendar year, and/or (iv) a highest number of consecutive days that a patient was not covered by their prescribed medication during a previous calendar year, and wherein the parameters of historical interventions include one or more of: (i) methods of contact that were used to schedule any interventions with a patient, or (ii) types of interventions that were attempted to be scheduled for a patient, and also include one or more of: (a) an indication of which interventions were successfully scheduled for the patient, (b) an indication of which interventions that were actually attended by the patient, or (c) a number of days, after an intervention actually attended by the patient, that the patient was covered by their prescribed medication;

training, by the processor, a prescription adherence machine learning model, using the training data, to predict a likelihood that a proportion of days that a patient, of a plurality of patients, will be covered by a prescribed medication over the calendar year will be below a threshold value, and parameters of interventions that are likely to be effective for the patient;

applying, by the processor, the trained prescription adherence machine learning model to prescription adherence data associated with the patient, to assign the patient to a risk profile group;

prioritizing, by the processor, each of the plurality of patients based on risk profile groups of each of the plurality of patients; and automatically attempting, by the processor, to contact each of the plurality of patients for intervention in an order based on the prioritizing.

2. The computer-implemented method of claim 1, wherein prescription adherence data further includes data indicating one or more of:

(i) a proportion of days, over a previous calendar year, that a patient was covered by the prescribed medication, and/or (ii) a number of days between a patient's actual first prescription fill date of the previous calendar year and an end of the previous calendar year.

3. The computer-implemented method of claim 1, further comprising:

selecting, by the processor, a mode of communication for attempting to contact the patient based on the risk profile group of the patient.

4. The computer-implemented method of claim 1, further comprising:

selecting, by the processor, a type of intervention based on the risk profile group of the patient.

5. The computer-implemented method of claim 1, wherein prioritizing each of the plurality of patients is further based on a number of failed contact attempts associated with each of the plurality of patients.

6. A computer system for using predictive modeling to improve patient adherence to prescription medication regimens, comprising:

one or more processors; and a non-transitory program memory communicatively coupled to the one or more processors and storing executable instructions that, when executed by the one or more processors, cause the computer system to:

generate training data using historical prescription adherence data and parameters of historical interventions to improve patient adherence to prescription medication regimens associated with a plurality of historical patients, and a corresponding proportion of days that each respective historical patient of the plurality of historical patients is covered by their respective prescribed medication over a calendar year, wherein the historical prescription adherence data includes data indicating one or more of: (i) a number of days between a patient's expected first prescription fill date of the calendar year and the patent's first prescription fill date of the calendar year, (ii) a month of a patient's first prescription fill date of the calendar year, (iii) a number of days' supply associated with a patient's first prescription fill date of the calendar year, and/or (iv) a highest number of consecutive days that a patient was not covered by their prescribed medication during a previous calendar year, and wherein the parameters of historical interventions include one or more of: (i) methods of contact that were used to schedule any interventions with a patient, or (ii) types of interventions that were attempted to be scheduled for a patient, and also include one or more of: (a) an indication of which interventions were successfully scheduled for the patient, (b) an indication of which interventions that were actually attended by the patient, or (c) a number of days, after an intervention actually attended by the patient, that the patient was covered by their prescribed medication;

train a prescription adherence machine learning model, using the training data, to predict a likelihood that a proportion of days that a patient, of a plurality of patients, will be covered by a prescribed medication over the calendar year will be below a threshold value, and parameters of interventions that are likely to be effective for the patient;

apply the trained prescription adherence machine learning model to prescription adherence data associated with the patient, to assign the patient to a risk profile group;

prioritize each of the plurality of patients based on risk profile groups of each of the plurality of patients; and automatically attempt to contact each of the plurality of patients for intervention in an order based on the prioritizing.

7. The computer system of claim 6, wherein prescription adherence data includes data indicating one or more of:

(i) a proportion of days, over a previous calendar year, that a patient was covered by the prescribed medication, and/or (ii) a number of days between a patient's actual first prescription fill date of the previous calendar year and an end of the previous calendar year.

8. The computer system of claim 6, wherein the executable instructions further cause the computer system to:

select a mode of communication for attempting to contact the patient based on the risk profile group of the patient.

9. The computer system of claim 6, wherein the executable instructions further cause the computer system to:

select a type of intervention based on the risk profile group of the patient.

10. The computer system of claim 6, wherein the executable instructions further cause the computer system to prioritize each of the plurality of patients based on a number of failed contact attempts associated with each of the plurality of patients.

11. A tangible, non-transitory computer-readable medium storing executable instructions for using predictive modeling to improve patient adherence to prescription medication regimens that, when executed by at least one processor of a computer system, cause the computer system to:

generate training data using historical prescription adherence data and parameters of historical interventions to improve patient adherence to prescription medication regimens associated with a plurality of historical patients, and a corresponding proportion of days that each respective historical patient of the plurality of historical patients is covered by their respective prescribed medication over a calendar year, wherein the historical prescription adherence data includes data indicating one or more of: (i) a number of days between a patient's expected first prescription fill date of the calendar year and the patent's first prescription fill date of the calendar year, (ii) a month of a patient's first prescription fill date of the calendar year, (iii) a number of days' supply associated with a patient's first prescription fill date of the calendar year, and/or (iv) a highest number of consecutive days that a patient was not covered by their prescribed medication during a previous calendar year, and wherein the parameters of historical interventions include one or more of: (i) methods of contact that were used to schedule any interventions with a patient, or (ii) types of interventions that were attempted to be scheduled for a patient, and also include one or more of: (a) an indication of which interventions were successfully scheduled for the patient, (b) an indication of which interventions that were actually attended by the patient, or (c) a number of days, after an intervention actually attended by the patient, that the patient was covered by their prescribed medication; and train a prescription adherence machine learning model using the training data, to predict a likelihood that a proportion of days that a patient, of a plurality of patients, will be covered by a prescribed medication over the calendar year will be below a threshold value, and parameters of interventions that are likely to be effective for the patient;

apply the trained prescription adherence machine learning model to prescription adherence data associated with the patient, to assign the patient to a risk profile group;

prioritize each of the plurality of patients based on risk profile groups of each of the plurality of patients; and automatically attempt to contact each of the patients for intervention in an order based on the prioritizing.

12. The tangible, non-transitory computer-readable medium of claim 11, wherein prescription adherence data includes data indicating one or more of:

(i) a proportion of days, over a previous calendar year, that a patient was covered by the prescribed medication, and/or (ii) a number of days between a patient's actual first prescription fill date of the previous calendar year and an end of the previous calendar year.

13. The tangible, non-transitory computer-readable medium of claim 11, further storing executable instructions that cause the computer system to:

select a mode of communication for attempting to contact the patient based on the risk profile group of the patient.

14. The tangible, non-transitory computer-readable medium of claim 11, further storing executable instructions that cause the computer system to:

select a type of intervention based on the risk profile group of the patient.

* * * * *